United States Patent [19]

Karami et al.

[11] Patent Number: 4,496,358
[45] Date of Patent: Jan. 29, 1985

[54] DIAPER HAVING VARIABLE DENSITY ABSORBENT PAD

[75] Inventors: Hamzeh Karami, Embourg; Myriam Delvaux, Hannut; Terence Cooper, Embourg, all of Belgium

[73] Assignee: Colgate-Palmolive Company, New York, N.Y.

[21] Appl. No.: 449,327

[22] Filed: Dec. 13, 1982

[51] Int. Cl.³ .............................................. A61F 13/16
[52] U.S. Cl. ..................................... 604/379; 604/381
[58] Field of Search ............... 604/379, 381, 365, 366, 604/367, 374, 375

[56] References Cited

U.S. PATENT DOCUMENTS

| | | | |
|---|---|---|---|
| 3,308,826 | 3/1967 | Blake | 604/381 X |
| 3,595,235 | 7/1971 | Jepersen | 604/381 X |
| 4,044,768 | 8/1977 | Mesek et al. | 604/381 |
| 4,223,677 | 9/1980 | Anderson | 604/381 |
| 4,282,874 | 8/1981 | Mesek | 604/365 |

Primary Examiner—John D. Yasko
Attorney, Agent, or Firm—Herbert S. Sylvester; Murray M. Grill; Norman Blumenkopf

[57] ABSTRACT

A disposable diaper comprising a top sheet, an absorbent pad assembly and a water impervious backing sheet. The absorbent pad assembly includes one or more absorbent pads at least one of which is treated with a water spray to vary the density thereof increasingly from top to bottom. The absorbent pad assembly may have a lower wadding sheet integrally stabilized to the pad treated with the water spray.

4 Claims, 3 Drawing Figures

DIAPER HAVING VARIABLE DENSITY ABSORBENT PAD

BACKGROUND OF THE INVENTION

1. Field of the Invention

This invention relates to disposable diapers and, more particularly, to a diaper with a density gradually decreasing from the bottom of the pad to the top thereof.

2. Description of the Prior Art

In U.S. Pat. No. 3,612,055 to Ripke, issued Jan. 29, 1970 for "Disposable Diaper and the Like and Method of Manufacture," there is disclosed a diaper having a paper-like cellulose layer which is densified below a batt of highly pourous material. U.S. Pat. No. 3,837,343 to Mesek et al, issued Sept. 24, 1974 for "Disposable Diaper, Fabric Useful Therein and Method of Manufacture," discloses a bonded fabric used with a binder in connection with diapers of the type disclosed in the previously recited patent. In U.S. Pat. No. 3,965,904 to Mesek et al, issued June 29, 1976 for "Disposable Diaper," further discloses mechanical variations of the foregoing patents especially with respect to the size of the batt and paper-like layer.

None of the foregoing patents or the prior art discloses the concept of varying the density of an absorbent pad by use of a water spray. Further, the lower wadding layer, as employed, is integrally stabilized to the absorbent pad to enable the absorbent pad assembly to resist tearing while receiving urine in depth.

SUMMARY OF THE INVENTION

It is, therefore, an object of the invention to provide an improved disposable diaper wherein the pad is highly resistant to tearing and wherein urine is distributed in a more optimum manner in depth to reduce surface wetness to the wearer.

The foregoing object and other ancillary objects and advantages of the invention are carried out according to the invention wherein the diaper is constructed employing a hydrophobic top sheet, an absorbent pad assembly and a water impervious bottom sheet. The absorbent pad assembly includes wadding having a top wadding layer and a bottom wadding layer. A water spray integrally stabilizes the tissue lower wadding layer to the absorbent pad to increase the resistance of the absorbent pad to tearing while varying the density of the pad increasingly from top to bottom. In embodiments employing a pair of absorbent pads, one of which may be embossed or compressed, the spray may be on the bottom of either pad or both. The configuration of the diaper may be box-pleated or contoured in style with or without elasticized crotch or waist band members or of any other conventional shape or style.

DETAILED DESCRIPTION OF THE INVENTION

Figure 1:
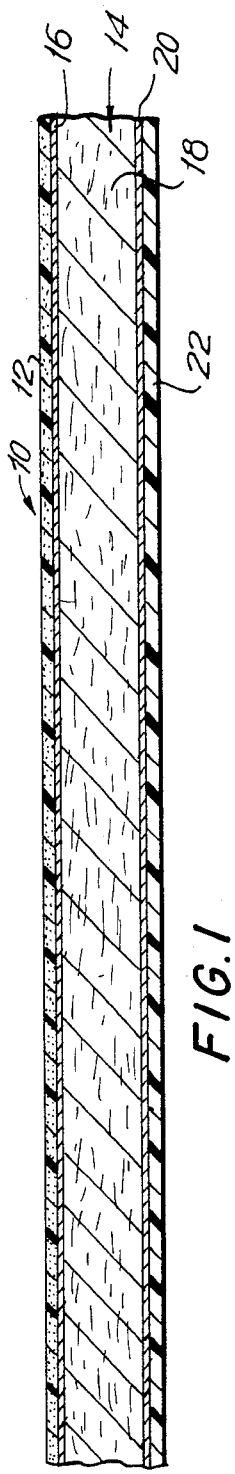
FIG. 1 is a sectional detail view of a disposable diaper according to the invention.

With continuing reference to the drawing wherein there is shown several embodiments of the invention, reference numeral 10 generally designates a disposable diaper. In all embodiments of the invention, the particular style or configuration is not controlling, the concept of this invention being equally applicable to any shape or style of disposable diaper whether contoured, of box-pleated configuration, flat rectangular, or any other well-known style or shape. The concept of this invention is also equally applicable whether the diaper has or does not have elasticized crotch or waistband members or special seals. Further, the precise materials used for the top sheet or backing sheet are by way of example only.

The diaper 10 comprises a top sheet 12 of hydrophobic material such as non-woven fibers of polyethylene or polypropylene or a combination thereof. The absorbent pad assembly 14 includes a top wadding sheet 16, an absorbent core 18 and a lower wadding sheet 20. The wadding sheets 16 and 20 may be in the form of a single sheet wrapped about the core 18 or otherwise constructed to envelope the core 18. The core 18 may be formed of wood fluff with or without super absorbent polymers or binders.

The bottom wadding sheet 20 may be treated with a surfactant to increase fiber wettability or may be given a hydrophobic treatment to increase wet strength. A bottom sheet 22 of water impervious plastic film, such as polyethylene or polypropylene film is employed.

In accordance with the concept of this invention, a spray of water in the order of 1 to 100 grams per square meter is applied between th- core 18 and the bottom wadding sheet. This water film sprayed between the bottom of the core 18 and the wadding sheet 20 stabilizes the core 18 and wadding sheet 20 together and makes an integrated layer in which density decreases from the bottom of the core 18 toward the top thereof, i.e. the density increases in the core as it extends away from the top sheet 12. This serves to improve spreading of urine resulting in improvement in the diaper dryness and the urine distribution in the diaper whereby the wet area at the top remains small.

Due to the integral stabilization of the bottom wadding sheet to the core 18, there is improved diaper integrity and resistance to tearing.

The spray solution may contain any suitable well-known binder and may be applied in a uniform manner or not. The spray may be more concentrated in the center, if desired, or may be discontinuous.

The entire pad assembly 14 may be bonded or stabilized to the top sheet 12 or bottom sheet 14 by stabilization glue lines such as cold or hot melt adhesives or the like.

Figure 2:
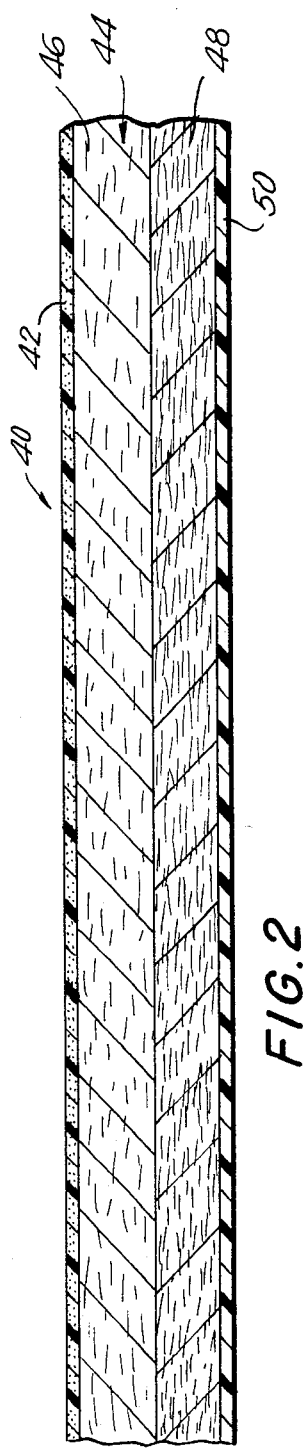
FIG. 2 is a view similar to FIG. 1, but showing a modified form of the invention employing two absorbent pads; and, FIG. 3 is a further modified form of the invention shown in a sectional detail view.

Referring now to the embodiment shown in FIG. 2, herein the diaper 40 has a top sheet 42 of a non-woven hydrophobic material, such as polyethylene or polypropylene fibers or a combination thereof. An absorbent dual pad assembly 44 underlies the top sheet 42 and includes a pair of absorbent pads 46 and 48. The lower absorbent pad 48 may be compressed to densify the wood fluff or like material of the pad 48 as compared to the pad 46. The pad 48 may be embossed at its undersurface in any pattern as desired.

A water impervious backing or bottom sheet 50 underlies the absorbent pad assembly 44. The bottom sheet 50 may be formed of polyethylene or polypropylene film.

A water spray is applied in the amount of from 1 to 100 grams per square meter either between the two layers or pads 46 and 48 or under bot pads 46 and 48. A binder solution mixed in the water spray will improve pad integrity. This water spray applied on the bottom of either pad 46 and/or 48 will form an integrated pad with the density decreasing from each pad 46, 48 from bottom to the top.

Figure 3:
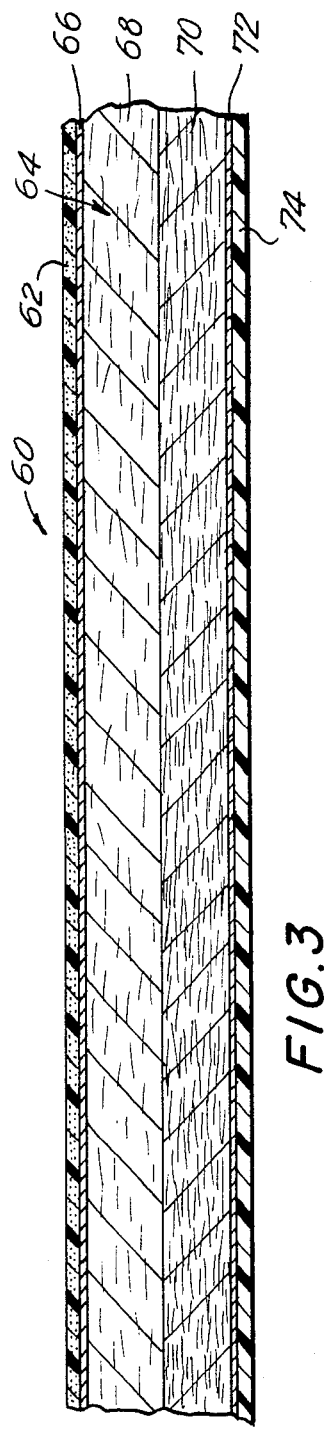

Referring now to FIG. 3, herein there is shown a diaper 60 including a top sheet of hydrophobic material, such as non-woven fibers of polyethylene or polypropylene. An absorbent dual pad assembly 64 underlies the top sheet and includes a top wadding sheet 66 which overlies the upper pad 68. The lower pad 70 may be compressed or embossed and overlies the bottom wadding sheet 72. A backing sheet 74 underlies the bottom wadding sheet 72.

A spray of water in the amount of 1 to 100 grams per square meter is applied between the bottom wadding sheet 72 and the lower pad. This serves to stabilize the lower wadding sheet 72 to the lower pad 70. Besides bonding the wadding sheet 72 to the pad 70, the density of the pad is further increased above the compression and/or embossing so that the density thereof decreases from its bottom to the top of the pad 70. Thus pad integrity and resistance to tearing is greatly increased. Further, a spray may be applied on the bottom surface of the pad 68, which serves to integrate the pad so that its density increases away from the top sheet 62.

A binder may be used in the water spray and glue lines of cold or hot melt adhesives or the like may be used to bond the absorbent dual pad assembly to the top sheet 62, the bottom sheet 74, or both.

What is claimed is:

1. A disposable diaper comprising, in order, a top sheet, an absorbent pad assembly including a fist absorbent pad, a second absorbent pad separate from said first pad and below said first pad, wadding means including an upper wadding layer above said first pad, and a lower wadding layer below said second pad, said wadding means enveloping both said pads, and a water impervious backing sheet, and water spray means integrally stabilizing said lower wadding layer to said second pad while varying the density of said second pad increasingly away from said top sheet.

2. A disposable diaper according to claim 1, wherein said water spray means is also between said first and second absorbent pads to also vary the density of said first pad while stabilizing said pads together.

3. A disposable diaper according to claim 1, wherein said water spray means is applied mainly in the center of said second pad.

4. A disposable diaper according to claim 1, wherein said top sheet is of hydrophobic material, said backing sheet being an imperforate plastic film.

* * * * *